United States Patent
Casasanta, III et al.

(10) Patent No.: US 9,616,013 B2
(45) Date of Patent: Apr. 11, 2017

(54) PHOTO-ACTIVATED HYDROGELS

(71) Applicant: L'Oreal, Paris (FR)

(72) Inventors: Vincenzo Casasanta, III, Woodinville, WA (US); William Brenden Carlson, Seattle, WA (US); Gregory David Phelan, Cortland, NY (US)

(73) Assignee: L'OREAL, Paris (FR)

( * ) Notice: Subject to any disclaimer, the term of this patent is extended or adjusted under 35 U.S.C. 154(b) by 67 days.

(21) Appl. No.: 14/582,824

(22) Filed: Dec. 24, 2014

(65) Prior Publication Data

US 2016/0184212 A1 Jun. 30, 2016

(51) Int. Cl.

| | | |
|---|---|---|
| C08G 69/00 | (2006.01) | |
| A61K 8/81 | (2006.01) | |
| A61K 8/04 | (2006.01) | |
| A61Q 19/08 | (2006.01) | |
| A61N 5/06 | (2006.01) | |
| A61K 8/86 | (2006.01) | |

(52) U.S. Cl.
CPC ............ *A61K 8/8158* (2013.01); *A61K 8/042* (2013.01); *A61K 8/86* (2013.01); *A61N 5/062* (2013.01); *A61N 5/0616* (2013.01); *A61Q 19/08* (2013.01); *C08G 69/00* (2013.01); *A61K 2800/81* (2013.01); *A61K 2800/95* (2013.01); *A61N 2005/066* (2013.01); *A61N 2005/0661* (2013.01); *A61N 2005/0662* (2013.01)

(58) Field of Classification Search
None
See application file for complete search history.

(56) References Cited

U.S. PATENT DOCUMENTS

| | | | | |
|---|---|---|---|---|
| 6,946,070 | B2 * | 9/2005 | Hammen ............... | B01D 15/00 210/198.2 |
| 2009/0164013 | A1 * | 6/2009 | Cruise .................... | A61L 27/16 623/11.11 |
| 2010/0047298 | A1 * | 2/2010 | Cassin ................... | A61K 8/891 424/401 |
| 2012/0145431 | A1 * | 6/2012 | Jeong ...................... | H01B 1/04 174/110 R |
| 2012/0289995 | A1 * | 11/2012 | Constant ............ | A61B 17/1214 606/200 |

(Continued)

FOREIGN PATENT DOCUMENTS

| | | |
|---|---|---|
| WO | 0 100 147 A2 | 2/1984 |
| WO | 01/68240 A2 | 9/2001 |
| WO | WO 0168240 A2 * | 9/2001 ............ B01D 15/00 |

OTHER PUBLICATIONS

Sigma Aldrich, Certificate of Analysis of Poly(ethylene glycol) Diacrylamide, dated Jun. 14, 2011S.*

(Continued)

*Primary Examiner* — Peter A Salamon
(74) *Attorney, Agent, or Firm* — Christensen O'Connor Johnson Kindness PLLC; Juan Zheng; Llewellyn Lawson (57) ABSTRACT

Presented herein are compositions and articles including a crosslinkable polymer that produces a crosslinked polymer upon exposure to light and/or heat. In some embodiments, the compositions are used to fill fine lines and wrinkles to provide a cosmetic benefit. In certain embodiments, the compositions and articles have desirable release properties for embedded materials.

19 Claims, 4 Drawing Sheets

(56) References Cited

U.S. PATENT DOCUMENTS

2016/0184212 A1* 6/2016 Casasanta, III ...... A61K 8/8158
604/20

OTHER PUBLICATIONS

Structure Search, STIC 14582824-EICSEARCH, pp. 1-117.*
International Search Report and Written Opinion mailed Feb. 12, 2016, issued in corresponding International Application No. PCT/US2015/062778, filed Nov. 25, 2015, 12 pages.

* cited by examiner

PHOTO-ACTIVATED HYDROGELS

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present disclosure features a composition, including a polymer of Formula (I)

(I)

wherein:

$R^1$, $R^2$, $R^3$, and $R^6$ are each independently selected from H and $C_{1-6}$ alkyl;

$R^4$ and $R^5$ are each independently selected from H, $C_{1-6}$ alkyl, $C_{1-6}$ haloalkyl, $C_{1-6}$ alkoxy, and $C_{1-6}$ haloalkoxy;

X is a multivalent linker selected from wherein $R^A$ and $R^B$ are each independently selected from H and $C_{1-6}$ alkyl;

$L^1$ is each independently —$C_{1-4}$ alkylene-O—;

n is each independently an integer from 0 to 10,000, provided that the sum of all n in Formula (I) is not 0; and m is 2, 3, or 4.

In another aspect, the present disclosure features a composition including a polymer of formula (II)

(II)

wherein:

$R^{1A}$, $R^{2A}$, $R^{3A}$, $R^{4A}$, $R^{9A}$, $R^{10A}$, $R^{11A}$, $R^{12A}$, $R^{13A}$, and $R^{14A}$ are each independently selected from H and $C_{1-6}$ alkyl;

$R^{5A}$, $R^{6A}$, $R^{7A}$ and $R^{8A}$ are each independently selected from H, $C_{1-6}$ alkyl, $C_{1-6}$ haloalkyl, $C_{1-6}$ alkoxy, and $C_{1-6}$ haloalkoxy;

$X^A$ is —$[(CR^C R^D)_{m1}O]_{m2}$—, wherein $R^C$ and $R^D$ are each independently selected from H and $C_{1-6}$ alkyl;

m1 is 1, 2, 3, or 4;

m2 is an integer of from 1 to 5000;

s is an integer of from 0 to 5000;

t is an integer of from 0 to 5000; and s+t is an integer of from 1 to 10,000.

In yet another aspect, the present disclosure features a composition including a polymer of Formula (III)

(III)

wherein x is an integer of from 0 to 20, y is an integer of from 1 to 50, z is an integer of from 0 to 20, and x+z is an integer of from 1 to 40.

In yet another aspect, the present disclosure features a composition a polymer of Formula (IV)

(IV)

In yet a further aspect, the present disclosure features a method of using any one of the compositions above, including applying the composition to a skin portion; and exposing the skin portion to light and/or heat to provide a crosslinked polymer.

DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein.

DETAILED DESCRIPTION

Polymeric compositions can be applied onto a skin portion to reduce the appearance of fine lines and wrinkles. For example, existing polymeric compositions based on siloxanes often require the mixing of two compounds (prior-to or during application) to allow for resin- and catalyst-based polymerization or cross-linking of the composition. These polymers can fill in and level wrinkles and can provide day-long smoothing cosmetic effect. However, because these siloxane compositions include polymerized or cross-liked materials, they exhibit a peeling or flaking effect after a few hours of wear and are often difficult to remove. Thus, there is a need for polymeric materials (e.g., cosmetic fillers and covers) that have desirable cosmetic effects and that are also easily removable. These polymeric materials have controllable properties that are also suitable for a variety of applications, such as in medicine, industry, biotechnology, energy storage, batteries, agriculture, chemical safety, and drug delivery. The present disclosure seeks to fulfill these needs and provides further related advantages.

Disclosed herein are stimuli-responsive compositions and/or articles that include polymers that are activatable using a particular type of stimulus. Also disclosed herein are methods of using the compositions and/or articles. Such stimuli-responsive compositions and/or articles are advantageous because their properties are controlled by the presence or absence of the stimulus. For example, some compositions and/or articles undergo a structural or compositional change when exposed to a stimulus that initiates or promotes a chemical reaction. In exemplary applications of the disclosed embodiments, a composition and/or article that is coupled with photonic skin care devices is especially advantageous, as the composition and/or article utilizes the energies generated by the skin care devices (e.g., in the form of light and/or heat) to provide beneficial cosmetic effects to a skin area to which the composition has been applied.

In some embodiments, the stimuli-responsive composition and/or articles of the present disclosure includes a polymer that is activatable using light and/or heat. When the composition and/or article is applied to a body portion (e.g., a skin portion) and exposed to light and/or heat, the polymer undergoes crosslinking to provide a crosslinked hydrophilic network that is stable to peeling or flaking, but that is easily removed from a body portion, for example, by scrubbing or brushing in the presence of water and a surfactant and/or an oil.

DEFINITIONS

At various places in the present specification, substituents of compounds of the disclosure are disclosed in groups or in ranges. It is specifically intended that the disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is also intended that a linking group definition encompasses both forward and reverse directions. For example, when a variable for a linking group is —C(O)NH— (an amide), it is intended that the amide encompasses both —C(O)NH— and —NHC(O)—. As another example, when a linking group is —C(O)O— (an ester), it is intended that the ester encompasses both —C(O)O— and —OC(O)—.

It is further appreciated that certain features of the disclosure, which are, for clarity, described in the context of separate embodiments, can also be provided in combination in a single embodiment.

Conversely, various features of the disclosure which are, for brevity, described in the context of a single embodiment, can also be provided separately or in any suitable subcombination.

As used herein, the expression "between XX and YY" refers to a range of from XX to YY that includes the endpoints XX and YY.

As used herein, "polymer" refers to a chemical compound that is the result of polymerization of two or more repeating constitutional units (e.g., five or more repeating constitutional units, 10 or more repeating constitutional units). As used herein, polymer includes oligomers, which include from two to about 10 constitutional units.

As used herein, the term "copolymer" refers to a polymer that is the result of polymerization of two or more different monomers. In some embodiments, the number and the nature of each constitutional unit are separately controlled in a copolymer. In some embodiments, the constitutional units are disposed in a purely random, an alternating random, a regular alternating, a regular block, or a random block configuration unless expressly stated to be otherwise. A purely random configuration can, for example, be: x-x-y-z-x-y-y-z-y-z-z-z . . . or y-z-x-y-z-y-z-x-x . . . . An alternating random configuration can be: x-y-x-z-y-x-y-z-y-x-z . . . , and a regular alternating configuration can be: x-y-z-x-y-z-x-y-z . . . . A regular block configuration has the following general configuration: . . . x-x-x-y-y-y-z-z-z-x-x-x . . . , while a random block configuration has the general configuration: . . . x-x-x-z-z-x-x-y-y-y-z-z-z-x-x-z-z-z- . . . .

As used herein, the term "substituted" or "substitution" is meant to refer to the replacing of a hydrogen atom with a substituent other than H. For example, an "N-substituted piperidin-4-yl" refers to replacement of the H atom from the NH of the piperidinyl with a non-hydrogen substituent such as, for example, alkyl.

As used herein, the term "alkyl" refers to a saturated hydrocarbon group which is straight-chained (e.g., linear) or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. In some embodiments, an alkyl group contains from 1 to about 30, from 1 to about 24, from 2 to about 24, from 1 to about 20, from 2 to about 20, from 1 to about 10, from 1 to about 8, from 1 to about 6, from 1 to about 4, or from 1 to about 3 carbon atoms.

As used herein, the term "alkylene" refers to a linking alkyl group.

As used herein, "alkenyl" refers to an alkyl group having one or more double carbon-carbon bonds. In some embodiments, the alkenyl group is linear or branched. Example alkenyl groups include ethenyl, propenyl, and the like. In some embodiments, an alkenyl group contains from 2 to about 30, from 2 to about 24, from 2 to about 20, from 2 to about 10, from 2 to about 8, from 2 to about 6, or from 2 to about 4 carbon atoms.

As used herein, "alkenylene" refers to a linking alkenyl group.

As used herein, "alkynyl" refers to an alkyl group having one or more triple carbon-carbon bonds. In some embodiments, the alkynyl group is linear or branched. Example alkynyl groups include ethynyl, propynyl, and the like. In some embodiments, an alkynyl group contains from 2 to about 30, from 2 to about 24, from 2 to about 20, from 2 to about 10, from 2 to about 8, from 2 to about 6, or from 2 to about 4 carbon atoms.

As used herein, "alkynylene" refers to a linking alkynyl group.

As used herein, "alkoxy" refers to an —O-alkyl group. Example alkoxy groups include methoxy, ethoxy, propoxy (e.g., n-propoxy and isopropoxy), t-butoxy, and the like.

As used herein, the term "vinyl moiety" refers to the functional group —CH═CH$_2$, which is optionally substituted.

As used herein, the term "aryl" refers to monocyclic or polycyclic (e.g., having 2, 3, or 4 fused rings) aromatic hydrocarbons such as, for example, phenyl, naphthyl, anthracenyl, phenanthrenyl, indanyl, and indenyl. In some embodiments, aryl groups have from 6 to about 20 carbon atoms. In some embodiments, an aryl group is a 5, 6, or 7-membered aromatic ring.

As used herein, the term "halo" or "halogen" includes fluoro, chloro, bromo, and iodo.

As used herein, the term "vinyl moiety" refers to the functional group —CH═CH$_2$, which is optionally substituted.

As used herein, "crosslink" refers to a bond, atom, or group of atoms that connects two adjacent chains of atoms in a large molecule such as a polymer. Internal crosslinking between two sites on a single molecule (e.g., a polymer) is also possible.

As used herein, "hydrogel" refers a substance formed when an organic hydrophilic polymer, (natural or synthetic) that is crosslinked via covalent, ionic, or hydrogen bonds to form a three-dimensional open-lattice network structure that entraps water molecules to form a gel. In some embodiments, hydrogels contains 90% or more water (e.g., 80% or more, 70% or more, 60% or more, or 50% or more) by volume.

As used herein, "molecular weight" of a polymer refers to a number average molecular weight ($M_n$) that is determined by titration, by vapor phase osmometry, or by gel permeation chromatography.

As used herein, the term "constitutional unit" of a polymer refers an atom or group of atoms in a polymer, including a part of the chain together with its pendant atoms or groups of atoms, if any. In some embodiments, the constitutional unit refers to a repeat unit. In some embodiments, the constitutional unit refers to an end group on a polymer chain. For example, in some embodiments, the constitutional unit of polyethylene glycol is —CH$_2$CH$_2$O— corresponding to a repeat unit, or —CH$_2$CH$_2$OH corresponding to an end group.

As used herein, the term "repeat unit" corresponds to the smallest constitutional unit, the repetition of which constitutes a regular macromolecule (or oligomer molecule or block).

As used herein, the term "end group" refers to a constitutional unit with only one attachment to a polymer chain, located at the end of a polymer. For example, in some embodiments, the end group is derived from a monomer unit at the end of the polymer, once the monomer unit has been polymerized. As another example, the end group is a part of a chain transfer agent or initiating agent that was used to synthesize the polymer.

As used herein, the term "terminus" of a polymer refers to a constitutional unit of the polymer that is positioned at the end of a polymer backbone.

As used herein, "amino acid" refers to an organic compound including a primary or secondary amine and a carboxylic acid functional group, with a side chain. Amino acids have a molecular weight of 500 or less. Non-limiting examples of natural amino acid include histidine, isoleucine, leucine, lysine, methionine, phenylalanine, threonine, tryptophan, valine, alanine, arginine, asparagine, aspartic acid, cysteine, glutamic acid, glutamine, glycine, ornithine, proline, selenocysteine, serine, tyrosine, selenocysteine, pyrrolysine, N-formylmethionine, etc. Non-limiting examples of non-natural amino acids include, for example, amino acid analogs such as azetidine-2-carboxylic acid, 3,4-dehydroproline, perthiaproline, canavanine, ethionine, norleucine, aminohexanoic acid, homoallylglycine, homopropargylglycine, etc. Non-limiting examples of non-natural amino acids also include sugar amino acids such as N-methyl-glucamine where amino and carboxyl functional groups have been incorporated into a sugar framework (e.g., at the two termini of regular 2,5 or 2,6-anhydro sugar frameworks). In some embodiments, the term "amino acid" also includes "amino acid residues," which are amino acids that are incorporated into a larger molecule, for example, by reaction of the amino or carboxylic acid functional groups with a reactive moiety. When the amino acid is incorporated into a larger molecule, what remains of the amino acid in the larger molecule is generally referred to as an "amino acid residue". For example, the amino acid residue can lack a hydrogen of the amino group, or a hydroxyl moiety of the carboxyl group, or both.

As used herein, "peptide" refers to a chain of amino acid monomers linked by amide bonds. In some embodiments, a peptide includes from 2 amino acid residues to 50 amino acids residues (e.g., from 2 to 20 amino acid residues, from 2 to 10 amino acid residues, or from 5 to 10 amino acid residues).

As used herein, "activatable" refers to a material that is capable of undergoing a structural or conformational change upon application of a stimulus. The structural or conformational change confers a change in a property, function, or appearance, in the material. For example, in some embodiments, a composition and/or article has a polymer that can be crosslinked when exposed to light and/or heat. When exposed to light and/or heat, the polymer undergoes crosslinking to provide a crosslinked network that can absorb water.

As used herein, the term "hydrophilic" refers to a moiety or a molecule that is attracted to and tends to be dissolved by water. The hydrophilic moiety is miscible with an aqueous phase. Hydrophilic molecules are polar and/or ionizable in aqueous conditions. In some embodiments, hydrophilic molecules are ionizable under aqueous conditions and/or contain polar functional groups such as amides, hydroxyl groups, or ethylene glycol residues. Examples of hydrophilic moieties include carboxylic acid groups, amino groups, hydroxyl groups, etc.

As used herein, the term "hydrophobic" refers to a moiety or a molecule that is not attracted to water with significant nonpolar surface area at physiological pH and/or salt conditions. Hydrophobic molecules or moieties tend to be non-polar in aqueous conditions. Examples of hydrophobic moieties include alkyl groups, aryl groups, etc.

As used herein, a "cosmetic composition" refers to a composition suitable for topical application on keratinous tissue.

As used herein, "keratinous tissue" refers to the keratin-containing layers disposed as the outermost protective covering of mammals which include, but are not limited to, skin, hair, nails, and cuticles.

As used herein, "effective amount" refers to an amount sufficient to induce one or more effects to the affected area. Non-limiting examples of effects include a change in skin appearance (e.g., decrease in wrinkles), a change in moisture retention of skin, a change in skin texture, etc.

As used herein, "improve skin condition" or "improving skin condition" includes to effecting a visually and/or tactilely perceptible positive change, or benefit, in skin appearance and feel. Benefits that are provided include, but are not limited to, one or more of the following: reducing the appearance of wrinkles, coarse deep lines, fine lines, crevices, bumps, and large pores; thickening of keratinous tissue (e.g., building the epidermis and/or dermis and/or subdermal layers of the skin, and where applicable, the keratinous layers of the nail and hair shaft, to reduce skin, hair, or nail atrophy); increasing the convolution of the dermal-epidermal border (also known as the rete ridges); preventing loss of skin or hair elasticity, for example, due to loss, damage and/or inactivation of functional skin elastin, resulting in such conditions as elastosis, sagging, loss of skin or hair recoil from deformation; reduction in cellulite; change in coloration to the skin, hair, or nails, for example, undereye circles, blotchiness (e.g., uneven red coloration due to, for example, rosacea), sallowness, etc.

As used herein, the term "signs of skin aging" includes all outward visibly and tactilely perceptible manifestations, as well as any macro- or micro-effects, due to keratinous tissue aging. These signs may result from processes which include, but are not limited to, the development of textural discontinuities such as wrinkles and coarse deep wrinkles, fine lines, skin lines, crevices, bumps, large pores, unevenness or roughness; loss of skin elasticity; discoloration (including undereye circles); blotchiness; sallowness; hyperpigmented skin regions such as age spots and freckles; keratoses; abnormal differentiation; hyperkeratinization; elastosis; collagen breakdown, and other histological changes in the stratum corneum, dermis, epidermis, vascular system (e.g., telangiectasia or spider vessels), and underlying tissues (e.g., fat and/or muscle), especially those proximate to the skin.

As used herein, "cosmetically acceptable" refers to a composition and/or article component that is safe for contact with a human integument.

As used herein, "physiological conditions" refer to a temperature range of about 37 degrees Celsius and a pH of about 7 (e.g., 7.3-7.4).

As used herein, "multivalent" refers to an atom or chemical moiety that forms bonds to two or more discrete moieties. For example, a carbon atom can form bonds to 2, 3, or 4 moieties and can be divalent, trivalent, or tetravalent, respectively.

Unless otherwise defined, all technical and scientific terms used herein have the same meaning as commonly understood by one of ordinary skill in the art. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Compositions and Articles Including Crosslinkable Polymers

In some embodiments, the compositions and/or articles of the present disclosure include a polymer that can be crosslinked to produce a crosslinked polymer. When the composition and/or article is applied to a skin portion and the polymer is crosslinked, the crosslinked polymer fills fine lines and wrinkles. The polymers are crosslinked using light and/or heat to provide a network that has increased molecular weight compared to the uncrosslinked polymer, the crosslinked network is capable of absorbing water and produces a mechanical leveling and filling effect.

The present disclosure provides, inter alia, a polymer of Formula (I)

wherein:
$R^1$, $R^2$, $R^3$, and $R^6$ are each independently selected from H and $C_{1-6}$ alkyl;
$R^4$ and $R^5$ are each independently selected from H, $C_{1-6}$ alkyl, $C_{1-6}$ haloalkyl, $C_{1-6}$ alkoxy, and $C_{1-6}$ haloalkoxy;
X is a multivalent linker selected from wherein $R^A$ and $R^B$ are each independently selected from H and $C_{1-6}$ alkyl;
$L^1$ is each independently —$C_{1-4}$ alkylene-O—;
n is each independently an integer from 0 to 10,000, provided that the sum of all n in Formula (I) is not 0; and
m is 2, 3, or 4.

In some embodiments, $R^1$, $R^2$, $R^3$, and $R^6$ are each independently selected from H and $C_{1-3}$ alkyl.

In some embodiments, $R^1$, $R^2$, and $R^3$ are each independently selected from H and $C_{1-3}$ alkyl.

In some embodiments, $R^1$, $R^2$, and $R^3$ are each independently selected from $C_{1-3}$ alkyl.

In some embodiments, $R^2$ and $R^3$ are each H and $R^1$ is $C_{1-3}$ alkyl.

In some embodiments, $R^2$ and $R^3$ are each H and $R^1$ is methyl.

In some embodiments, $R^1$, $R^2$, $R^3$, and $R^6$ are each H.

In some embodiments, $R^6$ is H.

In some embodiments, $R^6$ is $C_{1-3}$ alkyl.

In some embodiments, $R^4$ and $R^5$ are each independently selected from H and $C_{1-6}$ alkyl.

In some embodiments, $R^4$ and $R^5$ are each independently selected from H and $C_{1-3}$ alkyl.

In some embodiments, $R^4$ and $R^5$ are each independently H.

In some embodiments, $R^4$ and $R^5$ are each independently $C_{1-3}$ alkyl.

In some embodiments, $R^4$ and $R^5$ are each independently selected from H and methyl.

In some embodiments, X is a multivalent linker selected from

In some embodiments, $R^A$ and $R^B$ are each H.

In some embodiments, $R^A$ and $R^B$ are each independently selected from $C_{1-6}$ alkyl.

In some embodiments, $R^A$ and $R^B$ are each independently selected from H and methyl.

In some embodiments, $L^1$ is each $CH_2O$.

In some embodiments, $L^1$ is each $CH_2CH_2O$.

In some embodiments, n is each independently an integer of from 1 to 10,000.

In some embodiments, n is each independently an integer of from 2 to 10,000.

In some embodiments, n is each independently an integer of from 2 to 5,000.

In some embodiments, n is each independently an integer of from 2 to 2,500.

In some embodiments, m is 2 (i.e., X is a divalent linker).

In some embodiments, m is 4 (i.e., X is a tetravalent linker).

In some embodiments, the polymer is a dendrimer.

This disclosure also provides, inter alia, a composition including a polymer of Formula (I).

This disclosure also provides, inter alia, an article including a polymer of Formula (I).

This disclosure also provides, inter alia, a polymer of Formula (IV)

This disclosure also provides, inter alia, a composition including a polymer of Formula (IV).

This disclosure also provides, inter alia, an article including a polymer of Formula (IV).

This disclosure also provides, inter alia, a polymer of formula (II)

wherein:

$R^{1A}$, $R^{2A}$, $R^{3A}$, $R^{4A}$, $R^{9A}$, $R^{10A}$, $R^{11A}$, $R^{12A}$, $R^{13A}$, and $R^{14A}$ are each independently selected from H and $C_{1-6}$ alkyl;

$R^{5A}$, $R^{6A}$, $R^{7A}$ and $R^{8A}$ are each independently selected from H, $C_{1-6}$ alkyl, $C_{1-6}$ haloalkyl, $C_{1-6}$ alkoxy, and $C_{1-6}$ haloalkoxy;

$X^A$ is $-[(CR^CR^D)_{m1}O]_{m2}-$, wherein $R^C$ and $R^D$ are each independently selected from H and $C_{1-6}$ alkyl;

m1 is 1, 2, 3, or 4;

m2 is an integer of from 1 to 5000;

s is an integer of from 0 to 5000;

t is an integer of from 0 to 5000; and s+t is an integer of from 1 to 10,000.

In some embodiments, $R^{1A}$, $R^{2A}$, $R^{3A}$, $R^{4A}$, $R^{6A}$, $R^{7A}$, $R^{9A}$, $R^{10A}$, $R^{11A}$, $R^{12A}$, and $R^{14A}$ are each H.

In some embodiments, $R^{2A}$, $R^{3A}$, $R^{11A}$, and $R^{12A}$ are H and $R^{1A}$ and $R^{10A}$ are each $C_{1-6}$ alkyl.

In some embodiments, $R^{2A}$, $R^{3A}$, $R^{11A}$, and $R^{12A}$ are H and $R^{1A}$ and $R^{10A}$ are each methyl.

In some embodiments, $R^{5A}$, $R^{8A}$, and $R^{13A}$, are each methyl.

In some embodiments, $R^{6A}$, $R^{8A}$, and $R^{13A}$, are each methyl.

In some embodiments, $R^{6A}$, $R^{8A}$, and $R^{14A}$ are each methyl.

In some embodiments, $R^{4A}$ and $R^{9A}$ are each H or methyl.

In some embodiments, $R^{4A}$ and $R^{9A}$ are each H.

In some embodiments, $X^A$ is $-CH_2CH_2O-$.

In some embodiments, m2 is an integer of from 1 to 5000 (e.g., from 2 to 5000).

In some embodiments, s is an integer of from 1 to 5000 (e.g., from 2 to 5000).

In some embodiments, t is an integer of from 1 to 5000 (e.g., from 2 to 5000).

In some embodiments, s+t is an integer of from 1 to 10,000 (e.g., from 1 to 8,000, from 1 to 5,000, from 1 to 2,500, from 1 to 1,000, from 1 to 500, from 1 to 100, from 1 to 10, from 3 to 8,000, from 3 to 5,000, from 3 to 2,500, from 3 to 1,000, from 3 to 500, from 3 to 100, or from 3 to 10). In some embodiments, s+t is an integer of 1 or greater (e.g., 10 or greater, 100 or greater, 500 or greater, 1,000 or greater, or 2,500 or greater) and/or 5,000 or less (e.g., 2,500 or less, 1,000 or less, 500 or less, 100 or less, or 10 or less).

In some embodiments, each of s and t are independently an integer of from 0 to 5,000 (e.g., from 1 to 5,000, from 1 to 2,500, from 1 to 1,000, from 1 to 100, from 3 to 5,000, from 3 to 2,500, from 3 to 1,000, or from 3 to 100).

In some embodiments, m2 is an integer of from 0 to 5,000 (e.g., from 1 to 5,000, from 1 to 2,500, from 1 to 1,000, from 1 to 100, from 1 to 50, from 3 to 5,000, from 3 to 2,500, from 3 to 1,000, from 3 to 100, or from 3 to 50).

In some embodiments, s+t is an integer of from 1 to 40 (e.g., from 1 to 30, from 1 to 20, from 1 to 10, from 1 to 6, from 3 to 30, from 3 to 20, from 3 to 10, or from 3 to 6). In some embodiments, s+t is an integer of 1 or greater (e.g., 3 or greater, 6 or greater, 10 or greater, 20 or greater, 30 or greater) and/or 40 or less (e.g., 30 or less, 20 or less, 10 or less, 6 or less, or 3 or less).

In some embodiments, each of s and t are independently an integer of from 0 to 20 (e.g., from 1 to 20, from 2 to 20, from 2 to 10, or from 1 to 6)

In some embodiments, m2 is an integer of from 1 to 40 (e.g., from 1 to 30, from 1 to 20, from 1 to 15, from 2 to 40, from 2 to 30, from 2 to 20, from 2 to 15, from 9 to 40, from 9 to 30, from 9 to 20, from 9 to 15, from 12 to 40, from 12 to 30, from 12 to 20, or from 12 to 15).

This disclosure also provides, inter alia, a composition including a polymer of Formula (II).

This disclosure also provides, inter alia, an article including a polymer of Formula (II).

Example 1 and FIG. 1, below, describe the synthesis and characterization of acrylamide-terminated oligo/poly-ethylene glycol. Example 2 and FIG. 2, below, describe the synthesis and characterization of acrylamide-terminated tetravalent poly(ethylene glycol).

The present disclosure also provides, inter alia, a polymer of Formula (III):

(III)

wherein x is an integer of from 0 to 20,
y is an integer of from 1 to 50,
z is an integer of from 0 to 20, and
x+z is 1 or greater.

In some embodiments, x+z is an integer of from 1 to 40 (e.g., from 1 to 30, from 1 to 20, from 1 to 10, from 1 to 6, from 3 to 30, from 3 to 20, from 3 to 10, or from 3 to 6). In some embodiments, x+z is an integer of 1 or greater (e.g., 3 or greater, 6 or greater, 10 or greater, 20 or greater, 30 or greater) and/or 40 or less (e.g., 30 or less, 20 or less, 10 or less, 6 or less, or 3 or less).

In some embodiments, each of x and z are independently an integer of from 0 to 20 (e.g., from 1 to 20, from 2 to 20, from 2 to 10, or from 1 to 6)

In some embodiments y is an integer of from 1 to 40 (e.g., from 1 to 30, from 1 to 20, from 1 to 15, from 2 to 40, from 2 to 30, from 2 to 20, from 2 to 15, from 9 to 40, from 9 to 30, from 9 to 20, from 9 to 15, from 12 to 40, from 12 to 30, from 12 to 20, or from 12 to 15).

In some embodiments, the present disclosure provides a composition including a polymer of Formula (III).

This disclosure also provides, inter alia, an article including a polymer of Formula (II).

Example 3 and FIG. 3, below, describe the synthesis and characterization of acrylamide-terminated Jeffamine®.

In some embodiments, the polymer of Formula (I), Formula (II), or Formula (III) is crosslinked in the presence of a free-radical initiator and light and/or heat. In some embodiments, the light includes a wavelength of between 200 and 1300 nm (e.g., between 280 and 900 nm, between 280 and 700 nm, between 280 and 500 nm, between 280 and 450 nm, between 280 and 400 nm, between 280 and 350 nm, or between 300 and 450). In some embodiments, the polymer of Formula (I), Formula (II), or Formula (III) is crosslinkable in the presence of a free-radical initiator and heat. Polymerization of polymers using light and/or heat and a radical initiator is described, for example, in Odian, George G. *Principles of Polymerization*, 4$^{th}$ ed., Hoboken, N.J.: Wiley-Interscience, 2004, herein incorporated by reference in its entirety.

When the polymer of Formulas (I), (II), or (III) is crosslinked, the vinyl moieties at the termini of the polymers crosslink with one another via radical-initiated polymerization to form alkylene linkages as described, for example, in Odian, George G. *Principles of Polymerization*, 4$^{th}$ ed., Hoboken, N.J.: Wiley-Interscience, 2004, herein incorporated by reference in its entirety. In some embodiments, when the polymer is crosslinked, the polymer forms a film. In some embodiments, when the polymer is crosslinked, the crosslinked polymer is resistant to a water rinse at 50 psi or more (e.g., 40 psi or more, 30 psi or more, or 20 psi or more) and/or 55 psi or less (e.g., 50 psi or less, 40 psi or less, 30 psi or less, or 20 psi or less). In some embodiments, when the polymer is crosslinked, the crosslinked polymer has an elastic modulus that increases by 10% or more (e.g., 50% or more, 100% or more, 200% or more, 300% or more, or 400% or more) and/or 500% or less (e.g., 400% or less, 300% or less, 200% or less, 100% or less, or 50% or less) compared to an uncrosslinked polymer. In some embodiments, when the polymer is crosslinked, the polymer forms a hydrogel. In some embodiments, the hydrogel is in the form of a film. In an embodiment, hydrogel is in the form of a surface-attached hydrogel film. In some embodiments, the hydrogel absorbs up to 50% by volume of water. In some embodiments, the hydrogel absorbs water to provide a hydrogel having a water content of 75% or more (e.g., 80% or more, 85% or more, 90% or more, or 95% or more) by weight.

Crosslinkable polymers are also described, for example, in U.S. patent application Ser. No. 14/582,838, entitled "Photo-Activated Hydrogels", filed Dec. 24, 2014, herein incorporated by reference in its entirety.

The composition and/or article that includes the crosslinked polymer can be easily removed from a bodily portion to which the composition and/or article has been applied by scrubbing with an oscillating brush device using water and a surfactant. In an embodiment, a hydrogel film can be peeled off a surface.

As discussed above, this disclosure provides articles and compositions including a polymer of Formulae (I), (II), or (III). Examples of articles include medical devices, such as bandages, dressing, tissue scaffolds, cardiovascular devices (e.g., stents, endoprostheses, implants, lenses, medical films, etc.) In some embodiments, the polymer forms a portion of the article, such as a lining in a bandage or a dressing, or a coating on a medical device. In certain embodiments, the polymer forms the entirety of the article, such as a tissue scaffold.

In some embodiments, a composition and/or article that includes a polymer of Formulae (I), (II), or (III) is in the form of a blend that includes non-crosslinkable components (e.g., PEG, pigments, therapeutic agents, etc.) dispersed or otherwise contained within the blend. When the polymer of Formulae (I), (II), or (III) is crosslinked, the polymer forms a network that contains the non-crosslinkable components, where the non-crosslinkable components are enmeshed within the crosslinked polymeric network. Example 4, below, describes the crosslinking of acrylamide-functionalized polyethylene glycol in a blend.

In some embodiments, a composition that includes a polymer of Formula (I), Formula (II), or Formula (III) is a cosmetic composition. In some embodiments, the cosmetic composition is a homogeneous mixture. In some embodiments, the cosmetic composition is a cream, a powder, or a lotion.

In some embodiments, the composition is a skin humectant. In some embodiments, the composition further includes a colorant, for example, titanium oxide and/or iron oxide. Example 5, below, describes a pigmented photo-crosslinked hydrogel.

In some embodiments, the composition further includes a carrier (e.g., a lipophilic carrier such as mineral oil, oleic acid, etc.). In some embodiments, the cosmetic composition is a foundation, a blush, a highlighter, or a bronzer.

In some embodiments, the composition and/or article further includes a radical initiator, such as anthraquinone-2-sulfonic acid sodium salt or 4,4-azobis(4-cyanovaleric acid), in an amount sufficient to initiate a reaction. In some embodiments, the radical initiator is present in a composition and/or article in and amount of 0.01% or more (e.g., 0.05% or more, 0.1% or more, 0.3% or more, 0.5% or more, or 0.7% or more) and/or 1% or less (e.g., 0.7% or less, 0.5% or less, 0.3% or less, 0.1% or less, 0.05% or less) by mass.

Additional Components

In some embodiments, in addition to the polymers above, the composition and/or article includes any number of additional components, such as, but not limited to: active ingredients (e.g., cosmetic, dermatological, and/or pharmaceutical), alcohols, allergy inhibitors, amino acids, anti-acne agents (e.g., salicylic acid), anti-aging agents, antiseptics, antifungal agents, antiperspirants, analgesics, anti-hair loss agents, anti-wrinkle agents, antibacterial agents, anti-microbial agents, anti-oxidants, anti-inflammatory agents, burn healing agents, colorants (e.g., lakes, pigments, and the like), de-pigmentation agents, deodorants, dyes, emollient (e.g., glycerin, butylene glycol), excipients, fatty substances, fillers, film formers (e.g., dimethicone acrylate copolymer, ethylhexyl acrylate copolymer), fragrances, free radical scavengers, glycerin, glycerin monostearate, glycerin distearate, hair growth agents, hair conditioners, hair softeners, hair moisturizers, herbal extracts, humectants (e.g., hyaluronic acid, orotic acid, lipoprotein), insect repellants, medication, moisturizers, non-active carrier oils (e.g., triglycerides, silicone oils, mineral oils), oils, peptides, polypeptides, proteins, perfumes, pigments, preservatives, plasticizers, reflectants, sebum absorbers, skin lightening agents, sunscreens, surfactants, tanning agents, thickening agents (e.g., hydroxyethylcellulose, xanthan gum, carbomer), Vaseline, vasoconstrictors, vasodilators, vitamins (e.g., Vitamin A, Vitamin E), water, waxes, and/or combinations thereof.

In some embodiments, the composition and/or article includes other ingredients (e.g., cosmetic ingredients) such as, but not limited to, humectants, emollients, moisturizers, anti-wrinkle ingredients, concealers, matte finishing agents, pigments, colorants, proteins, anti-oxidants, bronzers, chelating agents, emulsifiers, ultraviolet (UV) absorbing agents, oil absorbing agents, anti-foam agents, anti-tack agents, thickeners, fragrances, preservatives, anti-microbials, fungistats, neutralizing agents, vitamins, plasticizers, cohesion agents, basifying and acidifying agents, fillers, solvents, and/or mixtures thereof.

In some embodiments, the composition and/or article contains additional ingredients such as alkalinizing agents, emulsifying agents, emollients, plasticizers, preservatives, humectants, moisturizing agents, solvents, tonicity agents, active ingredients suitable to provide anti-aging benefits, and/or mixtures thereof. Examples of preferred additional ingredients include glycerin.

In some embodiments, additional ingredients are added to the compositions and/or articles as detailed below.

Colorants or pigments: n some embodiments, the composition and/or article includes one or more powders (e.g., cosmetic powders), for example, calcium aluminum borosilicate, PMMA, polyethylene, polystyrene, methyl methacrylate crosspolymer, nylon-12, ethylene/acrylic acid copolymer, boron nitride, Teflon, silica, or the like. In some embodiments, the composition and/or article includes colorants or pigments to impart a desired color or effect, examples are inorganic pigments, organic pigments, and/or lakes. Exemplary inorganic pigments include, but are not limited to, metal oxides and metal hydroxides such as magnesium oxide, magnesium hydroxide, calcium oxide, calcium hydroxides, aluminum oxide, aluminum hydroxide, iron oxides ($\alpha$-$Fe_2O_3$, $\gamma$-$Fe_2O_3$, $Fe_3O_4$, FeO), red iron oxide, yellow iron oxide, black iron oxide, iron hydroxides, titanium dioxide, titanium lower oxides, zirconium oxides, chromium oxides, chromium hydroxides, manganese oxides, cobalt oxides, cerium oxides, nickel oxides and zinc oxides and composite oxides and composite hydroxides such as iron titanate, cobalt titanate and cobalt aluminate. Suitable inorganic pigments also include non-metal oxides such as alumina and silica, ultramarine blue (i.e., sodium aluminum silicate containing sulfur), Prussian blue, manganese violet, bismuth oxychloride, talc, mica, sericite, magnesium carbonate, calcium carbonate, magnesium silicate, aluminum magnesium silicate, silica, titanated mica, iron oxide titanated mica, bismuth oxychloride, and the like. Organic pigments include, but are not limited to, at least one of carbon black, carmine, phthalocyanine blue and green pigment, diarylide yellow and orange pigments, and azotype red and yellow pigments such as toluidine red, litho red, naphthol red and brown pigments, and combinations thereof.

"Lakes" generally refer to a colorant prepared from a water-soluble organic dye, (e.g., D&C or FD&C) which has been precipitated onto an insoluble reactive or adsorptive substrate or diluent. The term "D&C" as used herein means drug and cosmetic colorants that are approved for use in drugs and cosmetics by the FDA. The term "FD&C" as used herein means food, drug, and cosmetic colorants which are approved for use in foods, drugs, and cosmetics by the FDA. Certified D&C and FD&C colorants are listed in 21 C.F.R. §74.101 et seq. and include the FD&C colors Blue 1, Blue 2, Green 3, Orange B, Citrus Red 2, Red 3, Red 4, Red 40, Yellow 5, Yellow 6, Blue 1, Blue 2, Orange B, Citrus Red 2, and the D&C colors Blue 4, Blue 9, Green 5, Green 6, Green 8, Orange 4, Orange 5, Orange 10, Orange 11, Red 6, Red 7, Red 17, Red 21, Red 22, Red 27, Red 28, Red 30, Red 31, Red 33, Red 34, Red 36, Red 39, Violet 2, Yellow 7, Yellow 8, Yellow 10, Yellow 11, Blue 4, Blue 6, Green 5, Green 6, Green 8, Orange 4, Orange 5, Orange 10, Orange 11, and so on. Substrates suitable for forming lakes include, without limitation, mica, bismuth oxychloride, sericite, alumina, aluminum, copper, bronze, silver, calcium, zirconium, barium, and strontium, titanated mica, fumed silica, spherical silica, polymethylmethacrylate (PMMA), micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, nylon, silica silylate, silk powder, sericite, soy flour, tin oxide, titanium hydroxide, trimagnesium phosphate, walnut shell powder, and mixtures thereof. Suitable lakes include, without limitation, those of red dyes from the monoazo, disazo, fluoran, xanthene, or indigoid families, such as Red 4, 6, 7, 17, 21, 22, 27, 28, 30, 31, 33, 34, 36, and Red 40; lakes of yellow pyrazole, monoazo, fluoran, xanthene, quinoline, dyes or salt thereof, such as Yellow 5, 6, 7, 8, 10, and 11; lakes of violet dyes including those from the anthroquinone family, such as Violet 2, as well as lakes of orange dyes, including Orange 4, 5, 10, 11, and the like. Suitable lakes of D&C and FD&C dyes are defined in 21 C.F.R. §82.51.

In some embodiments, the coloring agents are surface treated, for example, to make the coloring agents more hydrophobic or more dispersible in a vehicle. In one embodiment, the surface of the coloring agents is, for example, covalently or ionically bound to an organic molecule or silicon-based molecule or is adsorbed thereto, or the coloring agents is physically coated with a layer of material. In certain embodiments, the surface treatment compound is attached to the coloring agents through any suitable coupling agent, linker group, or functional group (e.g., silane, ester, ether, etc). In some embodiments, the compound includes a hydrophobic portion which is selected from, for example, alkyl, aryl, allyl, vinyl, alkyl-aryl, aryl-alkyl, organosilicone, di-organosilicone, dimethicones, methicones, polyurethanes, silicone-polyurethanes, and fluoro- or perfluoro-derivatives thereof. Other hydrophobic modifiers include lauroyl lysine, isopropyl titanium triisostearate (ITT), ITT and dimethicone (ITT/dimethicone) cross-polymers, ITT and amino acid, ITT/triethoxycaprylylsilane crosspolymer, waxes (e.g., carnauba), fatty acids (e.g., stearates), HDI/trimethylol hexylactone crosspolymer, PEG-8 methyl ether triethoxysilane, aloe, jojoba ester, lecithin, perfluoroalcohol phosphate, and Magnesium Myristate (MM), to name a few.

In some embodiments, a pigment component includes an alkyl silane surface-treated colorant including an alumina substrate (e.g., platelet shaped) and a pigment, dye, or lake bonded to the alumina substrate by an alkyl silane surface treatment. In some embodiments, the alkyl silane is octylsilane, and is formed by treatment with triethoxy caprylylsilane. Non-limiting examples of such colorants include, but are not limited to, alumina/titanium dioxide/triethoxycaprylylsilane 1% (COVALUMINE™ Atlas White AS), alumina/D&C Red aluminum lake CTD/Triethoxycaprylylsilane 1% (COVALUMINE™ Red Rose AS), alumina/D&C red aluminum lake CTD/triethoxycaprylylsilane 1% (COVALUMINE™ Sonoma Red AS), alumina/black iron oxide CTD/triethoxycaprylylsilane 1% (COVALUMINE™ Sonoma Black AS), alumina/D&C red #6 aluminum lake CTD/triethoxycaprylylsilane 1% (COVALUMINE™ Fire Red AS), alumina/yellow iron oxide CTD/triethoxycaprylylsilane 1% (COVALUMINE™ sonoma yellow AS), alumina/D&C blue #1 aluminum lake CTD/triethoxycaprylylsilane 1% (COVALUMINE™ Astral Blue AS), alumina/carmine CTD/triethoxycaprylylsilane 1% (COVALUMINE™ Campari AS), alumina/yellow #5 CTD/triethoxycaprylylsilane 1% (COVALUMINE™ Sunburst AS), alumina/triethoxycaprylylsilane 1%, and combinations thereof, each of which is available from SENSIENT™ CosmeticTechnologies LCW.

In some embodiments, interference or pearl pigments are included in the composition and/or article. Interference or pearl pigments typically are formed of micas layered with about 50 to 300 nm films of $TiO_2$, $Fe_2O_3$, or $Cr_2O_3$ or the like. These include white nacreous materials, such as mica covered with titanium oxide or covered with bismuth oxychloride; and colored nacreous materials, such as titanium mica with iron oxides, titanium mica with ferric blue or chromium oxide, titanium mica with an organic pigment of the aforementioned type. In some embodiments, interference or pearl pigments are used collectively in an amount of less than 1.0 wt %. In some embodiments, the pearlescent component has a bismuth oxychloride based pearlescent ingredient or reflectance pearls. It is believed that bismuth oxychloride matches the skin's natural pearlescence more than compounds such as titanium oxide. However, other pearlescent ingredients may be used. In some embodiments, the pearlescent component is CHROMA-LITE, which is a combination of colored pigment bonded to BI-LITE 20 (bismuth oxychloride and mica) using calcium stearate.

In some embodiments, the composition and/or article includes cosmetically or pharmaceutically acceptable vehicles. In some embodiments, the vehicle includes a liquid, including a single phase, a dual-phase system, or an emulsion. Emulsions include oil-in-water, silicone-in-water, water-in-oil, water-in-silicone, and the like. When formulated as an emulsion, an emulsifier is typically included. Examples of cosmetically or pharmaceutically acceptable vehicles include volatile silicones (e.g., cyclopentasiloxane), hydrocarbons, ester oils, lower alcohols (e.g., ethanol, isopropyl alcohol, etc.), and water.

In some embodiments, the composition and/or article includes emollients. Examples of emollients include, but are not limited to, esters oils (e.g., the etherification product of an acid of the form $R^A(COOH)_{1-2}$ with an alcohol of the form $R^B(OH)_{1-3}$ where $R^A$ and $R^B$ are each independently linear, branched, or cyclic hydrocarbon groups, optionally containing unsaturated bonds, and having from 1 to 30 carbon atoms, preferably from 2 to 30 carbon atoms, and more preferably, from 3 to 30 carbon atoms, optionally substituted with one or more functionalities including hydroxyl, oxa, oxo, and the like. In some embodiments, at least one of $R^A$ and $R^B$ includes at least one aliphatic chain. The esters defined above include, without limitation, the esters of mono-acids with mono-alcohols, mono-acids with diols and triols, di-acids with mono-alcohols, and tri-acids with mono-alcohols. Other emollients include dimethicone. In some embodiments, humectants, such as glycerin and other C1-10 polyols or diols are also included.

In some embodiments, the composition and/or article includes fillers in an amount from about 1% to about 20% (e.g., from about 1% to about 10%) by weight of the final composition. Examples of fillers include, but are not limited to, silica, PMMA, nylon, alumina, barium sulfate, or any other filler typically used in such compositions.

In some embodiments, the composition and/or article includes film formers. Examples of polymeric film formers include cellulosics, polyolefins, polyvinyls, polacrylates, polyurethanes, silicones, silicone acrylates, polyamides, polyesters, fluoropolymers, polyethers, polyacetates, polycarbonates, polyimides, rubbers, epoxies, formaldehyde resins, and homopolymers and copolymers of any of the foregoing.

In some embodiments, the composition and/or article includes oils. Suitable non-limiting examples of oils for the oil phase (for example, in an emulsion) include natural and synthetic oils, including animal, vegetable, and petroleum oils; fatty acid triglycerides; fatty acid esters such as octyl palmitate, isopropyl myristate and isopropyl palmitate; ethers such as dicapryl ether; fatty alcohols such as cetyl alcohol, stearyl alcohol and behenyl alcohol; sterols; hydrocarbons such as isooctane, isododecane, isohexadecane, decane, dodecane, tetradecane, tridecane, $C_{8-20}$ isoparaffins, mineral oil, petrolatum, isoeicosane and polyisobutene; $C_{10-30}$ cholesterol/lanosterol esters; lanolin; and the like. Representative hydrocarbons include paraffinic hydrocarbons available from Exxon under the ISOPARS trademark, and from the Permethyl Corporation. In addition, $C_{8-20}$ paraffinic hydrocarbons such as $C_{12}$ isoparaffin (isododecane) manufactured by the Permethyl Corporation having the tradename PERMETHYL 99 A™ are also contemplated to be suitable. Various commercially available $C_{16}$ isoparaffins, such as isohexadecane (having the tradename PERMETHYL®) are also suitable. In some embodiments, silicone oils such as dimethicones, cyclic silicones, and polysiloxanes may also be included in the oil phase. In one embodiment, silicone oils are present in an amount less than about 5% by weight of the oil phase.

In some embodiments, the composition and/or article includes thickeners. Examples of suspending and thickening agents include silica gels, gums, clays, fumed silica, fatty acid soaps, and various hydrocarbon gels, and other ingredients that when incorporated into the formulation remain on the surface of keratinous tissues as disclosed in the *International Cosmetic Dictionary and Handbook* (12th Ed.), which is hereby incorporated by reference. In some embodiments, the composition and/or article includes viscosifying agents such as gellants. Examples of viscosifying agents include bentone, triglycerides, aluminum stearate, $C_{18}$-$C_{36}$ acid glycol esters, glyceryl tribehenate, glycerol monostearate, alginates, carbomers, celluloses, gums, carageenans, starches or silicates.

In some embodiments, the composition and/or article includes waxes. Examples of waxes include, but are not limited to, linear polyethylene, microcrystalline petroleum wax, carnauba wax, lignite wax, ouricouri wax, rice bran wax, castor wax, mortar wax, stearone, acrawax, bayberry wax, castor wax, Japan wax, ozokerite, beeswax, candelilla wax, petrolatum, ceresin wax, cocoa butter, illipe butter, esparto wax, shellac wax, ethylene glycol diesters or triesters of $C_{18}$-$C_{36}$ fatty acids, cetyl palmitate, paraffin wax, hard tallow, lanolin, lanolin alcohol, cetyl alcohol, glyceryl monostearate, sugarcane wax, jojoba wax, stearyl alcohol, silicone waxes, and combinations thereof.

It is understood to those skilled in the art that any other cosmetically acceptable ingredients, i.e., those included in the *CFTA Cosmetic Ingredient Dictionary*, 3rd Ed., may be used. Details on techniques for formulation and administration may be found in the latest edition of "Remington's Pharmaceutical Sciences" (Maack Publishing Co., Easton, Pa.).

Synthesis of Polymers (I), (II), and (III)

The novel polymers of the present disclosure can be prepared in a variety of ways known to one skilled in the art of organic synthesis. The polymers of the present disclosure can be synthesized using the methods as hereinafter described below, together with synthetic methods known in the art of synthetic organic chemistry or variations thereon as appreciated by those skilled in the art.

The polymers of this disclosure can be prepared from readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

The processes described herein can be monitored according to any suitable method known in the art. For example, product formation can be monitored by spectroscopic means, such as nuclear magnetic resonance spectroscopy (e.g., $^{1}$H or $^{13}$C) infrared spectroscopy, spectrophotometry (e.g., UV-visible), or mass spectrometry, or by chromatography such as high performance liquid chromatography (HPLC) or thin layer chromatography.

Preparation of polymers can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis,* 4th. Ed., Wiley & Sons, 2006, which is incorporated herein by reference in its entirety.

The reactions of the processes described herein can be carried out in suitable solvents which can be readily selected by one of skill in the art of organic synthesis.

Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

Resolution of racemic mixtures of compounds can be carried out by any of numerous methods known in the art. An example method includes fractional recrystallization using a "chiral resolving acid" which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Resolution of racemic mixtures can also be carried out by elution on a column packed with an optically active resolving agent (e.g., dinitrobenzoylphenylglycine). Suitable elution solvent composition can be determined by one skilled in the art.

The polymers of the disclosure can be prepared, for example, using the reaction pathways and techniques as described, for example, in Odian, George G. *Principles of Polymerization,* 4$^{th}$ Ed., Hoboken, N.J.: Wiley-Interscience, 2004, herein incorporated by reference in its entirety.

In some embodiments, the polymers of the present disclosure are synthesized by starting with a multivalent polymer having amine terminal groups. The amine terminal groups can be coupled to acrylic acid derivatives (e.g., acryloyl chloride, methacryloyl chloride, substituted acryloyl chloride, acrylic acid, methacrylic acid, or substituted acrylic acid) to form amide bonds. In some embodiments, the coupling reaction is performed under catalysis (e.g., base catalysis). In some embodiments, the acrylic acid derivatives are activated, for example, using N-hydroxysuccinimide. In some embodiments, the coupling reaction is performed in the presence of a coupling agent, such as a carbodiimide or the like.

In some embodiments, the polymer is incorporated into a composition and/or article by mixing with any additional components of the composition and/or article using a mechanical mixer, high shear rotary mixer, a stirring mixer, a container shaker, and/or ultrasonic agitation.

To make an article formed entirely of the polymer, in some embodiments, the polymer is inserted into a mold, crosslinked in the mold by applying a light and/or heat, and removed from the mold as a hydrogel.

To coat an article with the polymer, in some embodiments, a solution including the polymer and one or more solvents is sprayed, painted, or otherwise applied to an article, or to a portion of an article. The article is then dried to remove the solvents.

Methods of Use

This disclosure also features, inter alia, a method of using a composition and/or article including a polymer of Formula (I), Formula (II), or Formula (III), including applying the composition and/or article to a skin portion; and exposing the skin portion to light and/or heat to provide a crosslinked polymer. In some embodiments, the light and/or heat is generated by a device. In other embodiments, the light and/or heat is provided by sunlight.

In some embodiments, to hydrate a skin portion, the composition and/or article including a polymer of Formulae (I), (II), or (III) is applied to a skin portion, light and/or heat is then applied to crosslink the polymer. In some embodiments, washing or scrubbing by hand and/or using sonic cleansing devices removes the composition and/or article. The crosslinked polymer absorbs water to provide a film having a water content of 75% or more (e.g., 80% or more, 85% or more, 90% or more, or 95% or more) by weight.

In some embodiments, the compositions and/or article (e.g., cosmetic compositions) disclosed herein may be applied to one or more skin surfaces and/or one or more mammalian keratinous tissue surfaces as part of a user's daily routine or regimen. In some embodiments, the composition and/or article is used on an "as needed" basis. In some examples, an effective amount of the composition and/or article is applied to a target portion of the keratinous tissue or skin.

In some embodiments, the method includes a step identifying a skin surface for treatment with the composition and/or article for improving skin condition. In some embodiments, the skin surface is identified by the user or a third party such as a dermatologist, cosmetician, or other individual, or even by a combination of different individuals. Identification may be done, for example, by visual inspection of the skin surface in need of treatment.

In some embodiments, skin surfaces suitable for application of the composition and/or article include those not typically covered by clothing such as facial skin surfaces, hand and arm skin surfaces, foot and leg skin surfaces, and neck and chest skin surfaces (e.g., décolletage). For example, areas identified for application may include areas such as the forehead, perioral, chin, periorbital, nose, and/or cheek skin surfaces. In another example, the composition and/or article is applied to any facial skin care surface and/or any other skin surface identified as in need of treatment by the composition and/or article.

In some embodiments, the method includes a step of applying the composition and/or article to the skin surface, which may or may not have been previously identified. Many regimens exist for the application of the composition.

In some embodiments, the composition and/or article is applied as needed and/or at least once a day, twice a day, or on a more frequent daily basis. In some embodiments, the composition and/or article is applied over a period of, for example, between about 1 week and about 12 weeks, between about 4 weeks and about 12 weeks, and/or between about 4 weeks and about 8 weeks, over multiple months (i.e., 3-12 months) or multiple years. In some embodiments, when applied twice daily, the first and second applications are separated by at least 1 to about 12 hours. For example, the composition (e.g., cosmetic composition) is applied in the morning and/or in the evening before bed.

In some embodiments, a composition and/or article including the polymer is delivered to a body portion once the polymer of Formulae (I), (II), or (III) has already been crosslinked. For example, in one embodiment, a tissue scaffold containing a crosslinked polymer of Formulae (I), (II), or (III) is delivered a body portion to promote tissue growth. In some embodiments, the tissue scaffold is an implant, or is a portion of an implant. As another example, a drug-delivery composition and/or article including a crosslinked polymer of Formulae (I), (II), or (III) and one or more therapeutic agents is administered to a body portion and delivers the therapeutic agents over a desired time period of, for example, 1 day (e.g., 1 week, 2 weeks, 1 month, or 6 months) to 1 year (e.g., 6 months, 1 month, 2 weeks, or 1 week).

The following examples are provided to illustrate, not limit, the disclosure.

Examples

Acrylamide systems have low toxicity and are suitable for applications in the cosmetic and/or pharmaceutical fields. Without wishing to be bound by theory, it is believed that anthraquinone-2-sulfonic acid sodium salt is relatively low in toxicity. For example, the HIMS rating for anthraquinone-2-sulfonic acid sodium salt is 1-health; 0-flammability; 0-reactivity. Furthermore, anthraquinone-2-sulfonic acid sodium salt is water soluble and thus appropriate for hydrogel crosslinking Its absorbance spectrum shows a n-π* transition from 385 nm-440 nm but it is capable of generating a radical with light above 400 nm. Several functionalized hydrogels were cured using this initiator as discussed below.

Example 1

Figure 1:
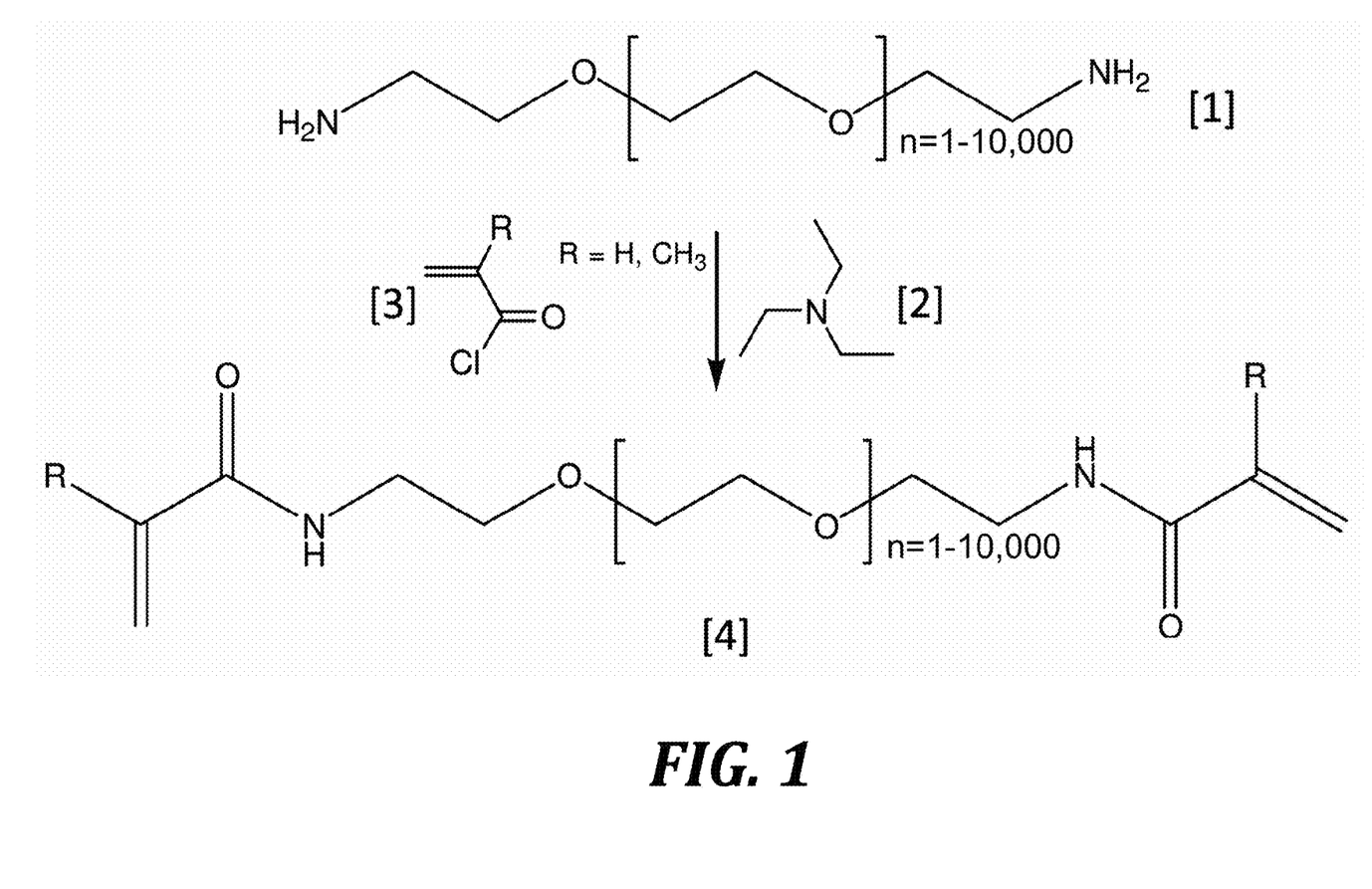
FIG. 1 is a scheme showing the synthesis of an embodiment of a polymer of the present disclosure.

Synthesis and Characterization of Acrylamide-Terminated Oligo/Poly-Ethylene Glycol FIG. 1 illustrates the synthesis of a PEG polymer that is functionalized by two acrylamide end groups. Referring to FIG. 1, poly(ethylene glycol) bis(amine) [1] (Aldrich, MW~2000, 1.0 g, 1 mmol NH$_2$ equivalents, LOT# MKBK4867V) was dissolved into 3.0 mL anhydrous chloroform in a three neck 25 mL round bottom flask equipped with stir bar and drying tube filled with anhydrous calcium chloride. To this solution was added 0.2 g (1.8 mmol) triethylamine [2] followed by 0.12 mL of acryloyl chloride [3] (1.5 mmol, Aldrich, LOT# SHBD4703V). The solution was allowed to stir for 3 hours and became a light yellow. The organic solvent and excess acryloyl chloride were then rotary evaporated. The solids were dissolved into a 3:1 chloroform-hexanes mixture and eluted on silica gel. The solvents were rotary evaporated to yield 1.1 g of poly (ethylene glycol) bis(acrylamide) [4] as a clear, colorless, odorless, viscous liquid. Proton NMR showed the ethyl ether protons of the PEG at 3.6 ppm. There were 40 repeat units which translates to approximately 160 ethyl ether protons. The acrylic protons are at 5.6 ppm, 6.1 ppm and at 6.4 ppm while the amide proton is at 8.3 ppm.

The resulting poly(ethylene glycol) bis(acrylamide) was dissolved into 4 mL of deionized water and ~0.1 g of anthraquinone-2-sulfonic acid sodium salt (0.3 mmol, Aldrich, LOT# MKBG0884V). The solution was spread over an acrylic block and exposed to blue illumination. The result was a cured film of poly(ethylene glycol) bis(acrylamide) that was resistant to rinse at tap water pressure.

Example 2

Synthesis and Characterization of Acrylamide-Terminated Tetravalent Poly(Ethylene Glycol)

Figure 2:
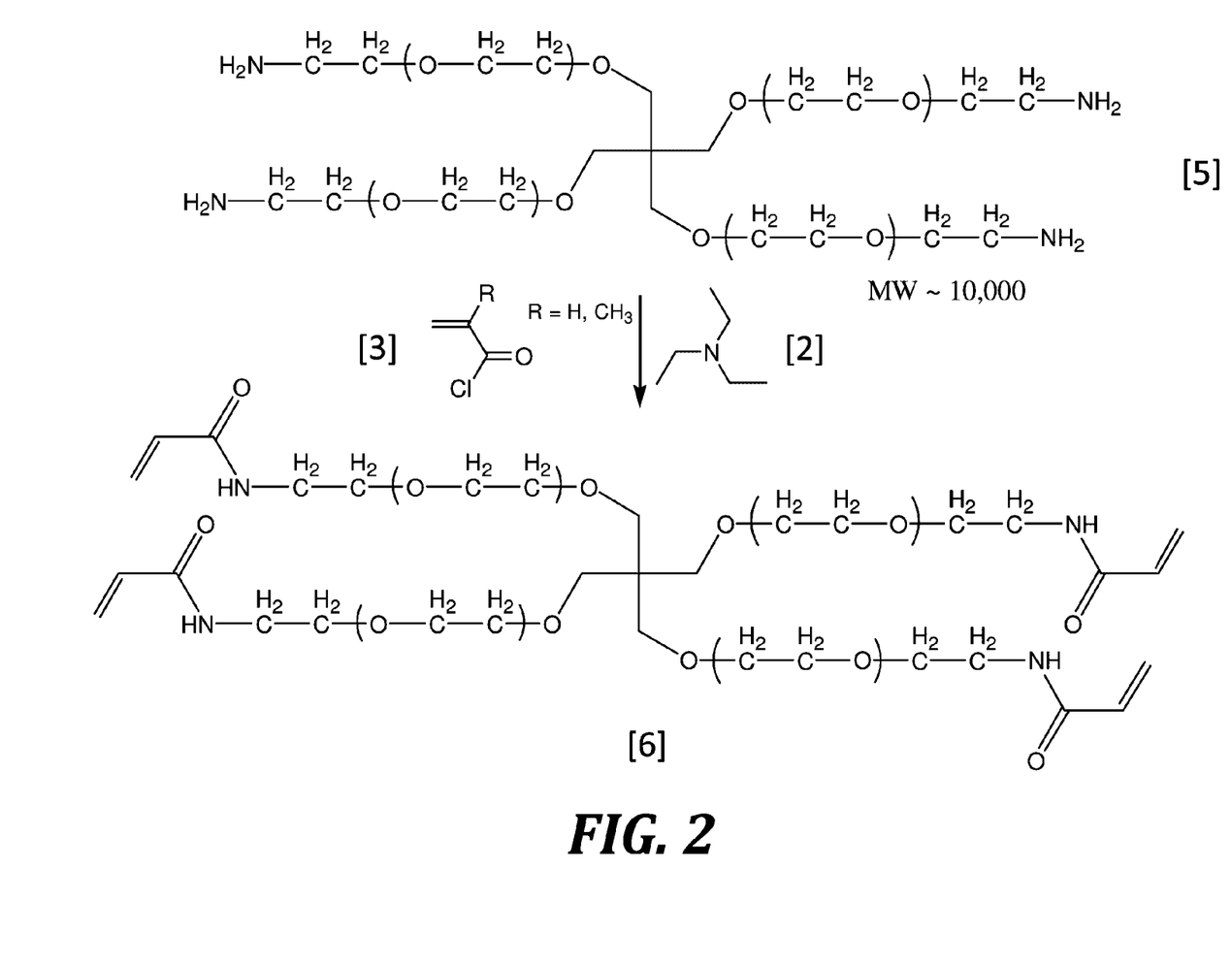
FIG. 2 is a scheme showing the synthesis of an embodiment of a polymer of the present disclosure.

Referring to FIG. 2, in a similar reaction setup as described in Example 1, a 4-arm, amine terminated poly (ethylene oxide), [5] (Aldrich, MW~10,000, 0.3 g, 0.12 mmol $NH_2$ equivalents) was dissolved into 2.5 mL anhydrous chloroform. To this solution was added 0.03 g (0.22 mmol) triethylamine [2] followed by 0.02 mL of acryloyl chloride [3] (0.2 mmol, Aldrich, LOT# SHBD4703V). The solution was allowed to stir for 3 hours under argon and remained colorless. The organic solvent and excess acryloyl chloride were then rotary evaporated. The solids were dissolved into a 3:1 chloroform-hexanes mixture and eluted on silica gel. The solvents were rotary evaporated to yield 0.3 g of poly(ethylene glycol) tetra(acrylamide) [6] as a clear, colorless, odorless, viscous liquid.

Example 3

Large-Scale Synthesis and Characterization of Acrylamide-Terminated Jeffamine®

Figure 3:
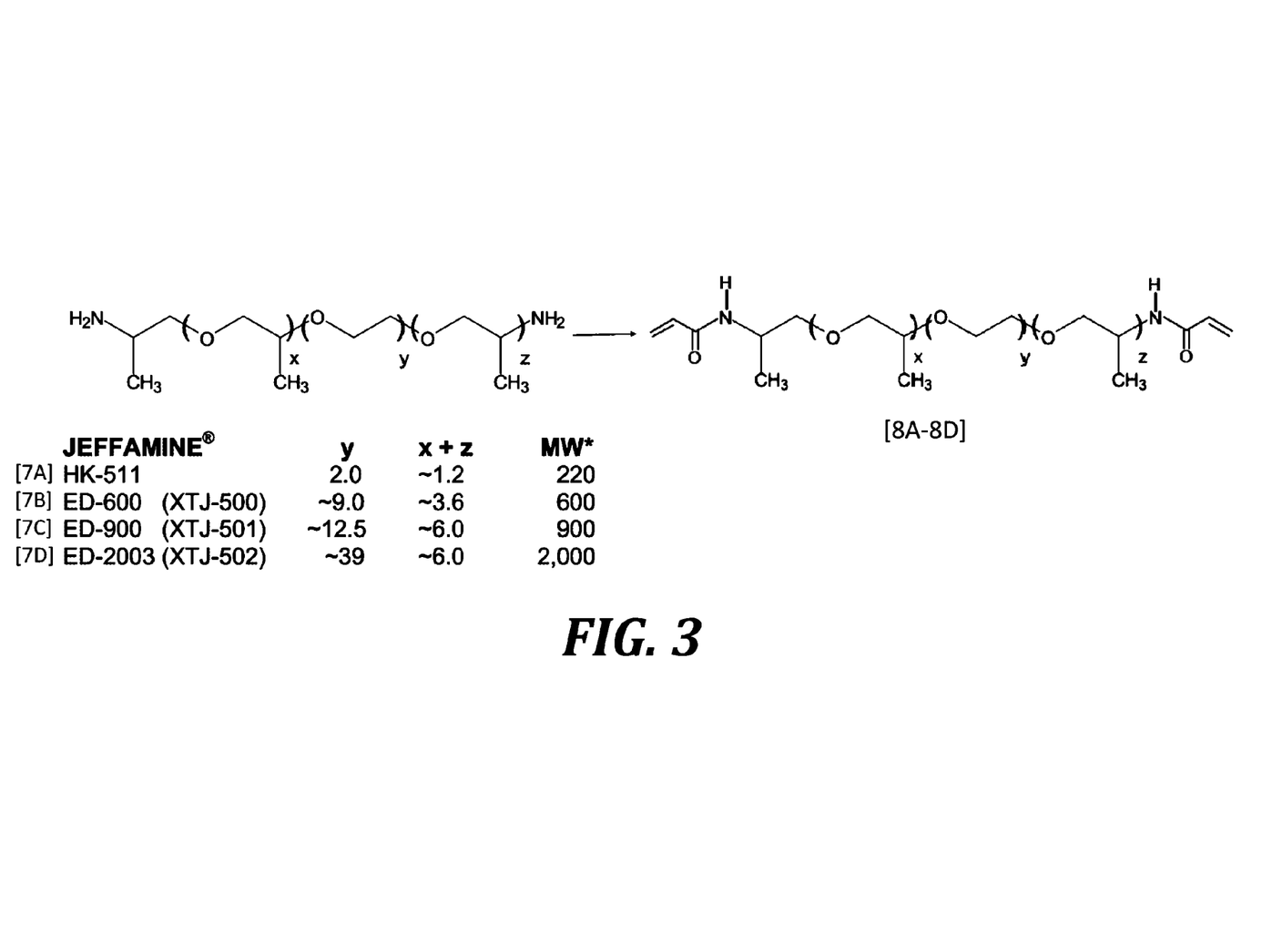
FIG. 3 is scheme showing the synthesis of an embodiment of a polymer of the present disclosure.
Figure 4:
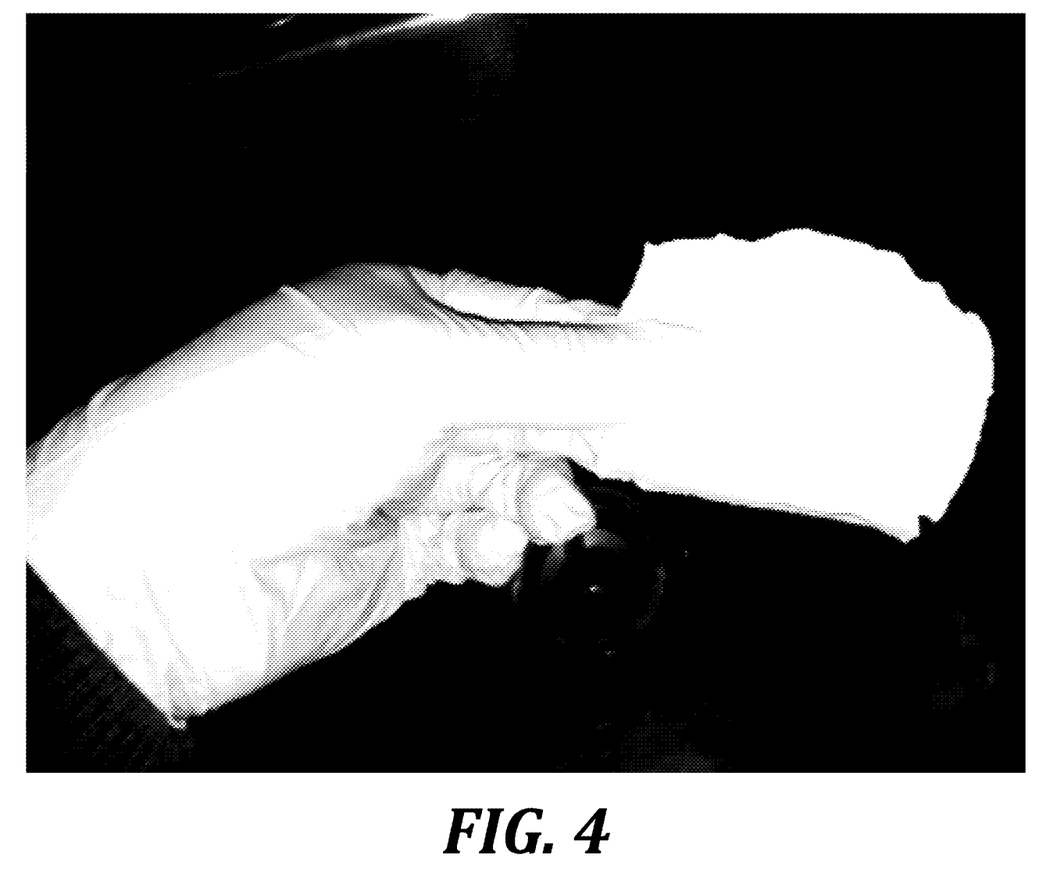
FIG. 4 is a photograph showing an embodiment of a crosslinked free-standing film of the present disclosure.

FIG. 3 illustrates the synthesis of acrylamide-terminated Jeffamine® [8A]-[8D]. the general synthetic procedure follows.

A 500.0 g quantity of Jeffamine ED-2003 (MW~1900, 0.53 mol amine equivalents, LOT#3F521) [7D] was added to 1000 mL water in a 3000 mL round bottom flask equipped with mechanical stirrer. After the Jeffamine dissolved, 45.0 g of potassium carbonate (0.33 mol) was added to the aqueous solution. The solution turned slightly cloudy and another 250 mL of water was added.

To 350 mL hexanes was added 58.8 g of acryloyl chloride (0.65 mol). The hexanes solution was then transferred to an addition funnel. The hexanes solution was then added dropwise to the slowly stirring aqueous solution of Jeffamine. The hexanes formed a layer on top of the water. The bi-phasic reaction was allowed to continue for 12 hours and the solution turned orange in color. The hexanes solution was then removed by separatory funnel. The water was removed by rotary evaporation using an azeotrope with acetone and denatured alcohol. The solids were dissolved into denatured alcohol and the insoluble potassium salts were filtered off. The denatured alcohol was then removed by rotary evaporation to yield an orange liquid final product [8D] which solidified when cooled.

The NMR of this product in $DCCl_3$ (below) showed carbamic acid (R—NH—C(=O)—OH) at 10.9 ppm, amide protons/HCCl3 at 7.2 ppm, acrylamide protons at 5.9 to 6.2 ppm, Jeffamine ethyl ether protons at 3.6 ppm, and methyl protons from the propylene oxide at 1.0 to 1.2 ppm. From the NMR it was determined that the Jeffamine ED-2003 consumed carbon dioxide from the potassium carbonate as it was formed. Thus, only ~25% of the amine groups were converted to acrylamides while 75% of them were converted to carbamic acid moieties.

Example 4

Crosslinking of Acrylamide-Functionalized Polyethylene Glycol in a Blend

A series of solutions was made to evaluate the crosslinking capabilities of blends of non-crosslinkable filler polymeric materials and the acrylamide-functionalized polyethylene glycol of Example 1. The non-crosslinkable polymeric material was dimethyl-terminated polyethylene glycol of 2 kDa molecular weight. The general procedure involved the dissolution of the acrylamide-functionalized PEG into water in the ratios shown in Table 1, below. To the water solution was added the dimethyl terminated PEG followed by 0.5% anthraquinone-2-sulfonic acid sodium salt as the photo-initiator. The solutions were drawn down on an acrylic block and exposed to 365 nm light. All ratios formed free-standing hydrogel films except for the lowest concentration functionalized example (0.426 g PEG-acrylamide).

TABLE 1

Blend composition and film forming properties.

| Run | PEG-Acrylamide | PEG-Dimethyl | Water | Sucessful film |
| --- | --- | --- | --- | --- |
| 1 | 4.256 g | 0 | 8.634 g | Yes |
| 2 | 3.598 g | 3.426 g | 9.045 g | Yes |
| 3 | 2.561 g | 3.612 g | 8.214 g | Yes |
| 4 | 1.236 g | 4.245 g | 9.045 g | Yes |
| 5 | 0.868 g | 4.097 g | 8.847 g | Yes |
| 6 | 0.426 g | 4.298 g | 8.839 g | No |

Example 5

Pigmented Photo-Cured Hydrogel

Acrylamide terminated PEG (4.3 g) of Example 1 was dissolved into deionized water (5.8 g). The polymer and water were well blended together to provide a homogeneous mixture.

To this mixture was added 0.05 g of anthraquinone-2-sulfonic acid sodium salt as the photo-initiator. 2.3 g of mineral foundation (a mixture of red, yellow, and black iron oxide and with white titania) was then added. The mixture was mixed at 1000 rpm using a small impeller blade for 5 minutes. The mixture was drawn down on an acrylic sheet at a thickness of 0.007". This layer was exposed to a 400 nm light source for 40 seconds and result was a free-standing pigmented hydrogel film.

While illustrative embodiments have been illustrated and described, it will be appreciated that various changes can be made therein without departing from the spirit and scope of the disclosure.

The embodiments of the disclosure in which an exclusive property or privilege is claimed are defined as follows:

1. A composition, comprising a polymer of Formula (I)

wherein:
$R^1$, $R^2$, $R^3$, and $R^6$ are each independently selected from H and $C_{1-6}$ alkyl;
$R^4$ and $R^5$ are each independently selected from H, $C_{1-6}$ alkyl, $C_{1-6}$ haloalkyl, $C_{1-6}$ alkoxy, and $C_{1-6}$ haloalkoxy;
X is a multivalent linker selected from wherein $R^A$ and $R^B$ are each independently selected from H and $C_{1-6}$ alkyl;
$L^1$ is each independently —$C_{1-4}$ alkylene-O—;
n is each independently an integer from 0 to 10,000, provided that the sum of all n in Formula (I) is not 0; and
m is 2, 3, or 4.

2. The composition of claim 1, wherein $R^1$, $R^2$, $R^3$, and $R^6$ are each independently selected from H and $C_{1-3}$ alkyl.

3. The composition of claim 1, wherein $R^1$, $R^2$, $R^3$, and $R^6$ are each H.

4. The composition of claim 1, wherein X is a multivalent linker selected from

5. The composition of claim 1, wherein $L^1$ is each $CH_2O$.
6. The composition of claim 1, wherein n is each independently an integer of from 2 to 5,000.
7. The composition of claim 1, wherein m is 2.
8. The composition of claim 1, wherein m is 4.
9. A composition, comprising a compound of Formula (IV).

10. The composition of claim 1, wherein the polymer is crosslinkable in the presence of a free-radical initiator and light.
11. The composition of claim 10, wherein when the polymer is crosslinked, the polymer forms a film.
12. The composition of claim 10, wherein when the polymer is crosslinked, the polymer forms a hydrogel.
13. The composition of claim 12, wherein the hydrogel absorbs up to 50% by volume of water.
14. The composition of claim 1, wherein the composition is a cosmetic composition.
15. The composition of claim 14, wherein the cosmetic composition is a homogeneous mixture.
16. The composition of claim 14, wherein the cosmetic composition is a cream, a powder, or a lotion.
17. The composition of claim 14, wherein the cosmetic composition is a foundation, a blush, a highlighter, or a bronzer.
18. A method of using a composition of claim 1, including:
applying a composition of claim 1 to a skin portion; and
exposing the skin portion to light to provide a crosslinked polymer.
19. The method of claim 18, wherein the light includes a wavelength between 200 and 1300 nm.

* * * * *